(12) United States Patent
Sijbers et al.

(10) Patent No.: US 12,350,008 B2
(45) Date of Patent: Jul. 8, 2025

(54) DETERMINATION OF PARAMETRIZED CHARACTERISTICS OF A TISSUE

(71) Applicants: IMEC VZW, Leuven (BE); UNIVERSITEIT ANTWERPEN, Antwerp (BE)

(72) Inventors: Jan Sijbers, Antwerp (BE); Ben Jeurissen, Antwerp (BE)

(73) Assignee: IMEC VZW, Leuven (BE)

( * ) Notice: Subject to any disclaimer, the term of this patent is extended or adjusted under 35 U.S.C. 154(b) by 1170 days.

(21) Appl. No.: 15/734,026

(22) PCT Filed: Apr. 26, 2019

(86) PCT No.: PCT/EP2019/060807
§ 371 (c)(1),
(2) Date: Dec. 1, 2020

(87) PCT Pub. No.: WO2019/228719
PCT Pub. Date: Dec. 5, 2019

(65) Prior Publication Data
US 2021/0212567 A1 Jul. 15, 2021

(30) Foreign Application Priority Data
Jun. 1, 2018 (EP) .................................... 18175610

(51) Int. Cl.
*A61B 5/00* (2006.01)
*A61B 5/055* (2006.01)
(Continued)

(52) U.S. Cl.
CPC ............ *A61B 5/0042* (2013.01); *A61B 5/055* (2013.01); *A61B 5/4064* (2013.01);
(Continued)

(58) Field of Classification Search
CPC .. A61B 5/055; A61B 5/4064; G01R 33/5608; G01R 33/56341; G06T 3/4053; G06T 2210/41
See application file for complete search history.

(56) References Cited

U.S. PATENT DOCUMENTS

| 8,811,706 B2 * | 8/2014 | Jensen .............. G01R 33/56341 382/128 |
| 9,709,651 B2 * | 7/2017 | Wong ............... G01R 33/56341 |

(Continued)

OTHER PUBLICATIONS

International Search Report and Written Opinion from PCT Application No. PCT/EP2019/060807, Jul. 23, 2019.

(Continued)

*Primary Examiner* — Christopher Koharski
*Assistant Examiner* — Helene Bor
(74) *Attorney, Agent, or Firm* — Workman Nydegger (57) ABSTRACT

Example embodiments describe a computer implemented method for obtaining parameterized characteristics of a tissue comprising obtaining at least two weighted MRI volume scans of the tissue, and transforming the two weighted MRI volume scans into parameters of a parameterized voxel-based model of the tissue by combined performing, by a super-resolution imaging technique, constructing a volume comprising voxels of the parameterized voxel-based model, and, by a quantitative MRI modelling technique, constructing the parameters for the respective voxels of the parameterized voxel-based model.

12 Claims, 7 Drawing Sheets

(51) Int. Cl.
 *G01R 33/56* (2006.01)
 *G01R 33/563* (2006.01)
 *G06T 3/4053* (2024.01)

(52) U.S. Cl.
 CPC ... *G01R 33/5608* (2013.01); *G01R 33/56341* (2013.01); *G06T 3/4053* (2013.01); *G06T 2210/41* (2013.01)

(56) References Cited

U.S. PATENT DOCUMENTS

| | | | | |
|---|---|---|---|---|
| 2003/0031351 | A1* | 2/2003 | Yim | G06V 10/457 382/130 |
| 2015/0253410 | A1* | 9/2015 | Warfield | G01R 33/5602 324/309 |
| 2016/0042508 | A1* | 2/2016 | Novikov | G06T 7/0012 382/131 |
| 2016/0231410 | A1* | 8/2016 | Warfield | G01R 33/5608 |
| 2016/0334489 | A1* | 11/2016 | Sperl | G01R 33/5608 |
| 2018/0329006 | A1* | 11/2018 | Haldar | G01R 33/543 |

OTHER PUBLICATIONS

Extended European Search Report from corresponding Application No. EP18175610.7, Nov. 7, 2018.

Jeurissen et al., "Multi-tissue Constrained Spherical Deconvolution for Improved Analysis of Multi-shell Diffusion MRI Data", NeuroImage, vol. 103, Aug. 7, 2014, pp. 411-426.

Sotiropoulos et al.,"RubiX: Combining Spatial Resolutions for Bayesian Inference of Crossing Fibers in Diffusion MRI", IEEE Transactions on Medical Imaging, vol. 32, No. 6, May 29, 2013, pp. 969-982.

Van Steenkiste et al., "Super-Resolution Reconstruction of Diffusion Parameters from Diffusion-Weighted Images with Different Slice Orientations", Magnetic Resonance in Medicine, vol. 75, No. 1, Jan. 22, 2015, pp. 181-195.

* cited by examiner

DETERMINATION OF PARAMETRIZED CHARACTERISTICS OF A TISSUE

FIELD OF THE INVENTION

The present invention generally relates, amongst others, to a method and related apparatus for obtaining parameterized characteristics of a tissue, like, for example, a brain tissue.

BACKGROUND OF THE INVENTION

A tissue is a cellular organizational level between cells and a complete organ in a human or animal body. It is a group of similar cells with an extracellular matrix, which together perform a specific function. Tissues may be classified depending on the origin of the cells, like, for example, muscle tissues, or nervous tissues and brain tissues.

The study of tissues, such as histology, or when related to diseases, histopathology, is used for the refinement of medical diagnosis and prognosis. For this, data is extracted from the tissues, for which a variety of techniques exists.

A known technique for obtaining data from a tissue, such as a brain tissue, is diffusion-weighted magnetic resonance imaging, dMRI, which is an in-vivo and non-invasive imaging technique. In a dMRI scanning operation, the presence of diffusion of water-molecules in the examined tissue is used to generate a contrast in magnetic resonances images resulting in diffusion-weighted, DW, images. The DW images are further processed to describe properties of the tissue. For example, for a brain tissue, the DW images are indicative for the presence of white matter, WM, gray matter, GM, and/or cerebrospinal fluid, CSF, and properties thereof, like, for example, an orientation distribution function of WM.

Since dMRI scanning operations are performed in clinical situations, there is a trade-off between acquisition time, spatial resolution of the images and signal-to-noise ratio, SNR, of these images. For example, a high SNR may be reached by a long acquisition time, however the time needed therefore may not be available, or, as another example, the equipment may not support high resolution images, through which the trade-off may be leveraged by enhancing the SNR and/or the acquisition time.

The trade-off between spatial resolution, SNR and acquisition time may be improved by using a super-resolution reconstruction technique, as described in Van Steenkiste, G., et al. 'Super-resolution reconstruction of diffusion parameters from diffusion-weighted images with different slice orientations.' *Magn. Reson. Med.* 75, 181-195 (2016). Herein, low-resolution DW images are combined into high-resolution quantitative parameters by minimizing least square differences between obtained low-resolution DW images and low-resolution DW images predicted from high-resolution parameters by solving a nonlinear least squares problem without constraints. These high-resolution quantitative parameters describe a diffusion tensor model indicative for properties of the tissue. In this method, the trade-off is improved by acquiring data with thick slices, which results in a reduced acquisition time and an increased SNR, whilst recovering the resolution along the slice direction through super-resolution reconstruction.

A drawback of this method is that the diffusion tensor model it builds on, is too simple to accurately describe an underlying microstructure. In particular, it does not model different microscopic compartments and does not model multiple underlying fibre orientations within a single voxel. This leads to ambiguity when relating the diffusion tensor parameters to the underlying histopathology.

Another drawback of this method is that it requires first and second order partial derivatives of the cost function, which comprises both the diffusion tensor model of the tissue and a mapping between high and low-resolution imaging voxels. In particular, the Hessian matrix for the second-order partial derivatives will become infeasible to store and calculate when more parameters with respect to the diffusion tensor model are calculated. Another drawback is that it does not readily support quantitative models with different functional forms or with arbitrary constraints.

Another way to obtain data from a tissue is by a quantitative MRI modelling technique as disclosed in Jeurissen, B. et al. 'Multi-tissue constrained spherical deconvolution for improved analysis of multi-shell diffusion MRI data.' *Neuroimage* 103, 411-426 (2014). In contrast to the diffusion tensor model used in the above super-resolution reconstruction technique, this model comprises multiple compartments and may resolve multiple fibre orientations within a single voxel. In this method, a multi-compartment spherical deconvolution operation is performed per voxel separately, resulting in more parameters per voxel compared to the diffusion tensor model in the above high-resolution reconstruction technique. The problem is solved as a linear least squares problem with linear constraints using quadratic programming. However, since this spherical deconvolution technique comprises an imposition of linear inequality constraints, this technique is unsuitable when the constraints are imposed on high resolution images, since this leads to an optimization problem that converges too slowly.

SUMMARY OF THE INVENTION

It is an object of the present disclosure to alleviate the above drawbacks and to provide an improved solution for obtaining high-resolution parameters describing a tissue with a low acquisition time, a high spatial resolution and a high SNR.

This object is achieved, in a first aspect, by a computer implemented method for obtaining parameterized characteristics of a tissue comprising:
  obtaining at least two weighted MRI volume scans of the tissue; and
  transforming the two weighted MRI volume scans into parameters of a parameterized voxel-based model of the tissue by combined performing, by a super-resolution imaging technique, constructing a volume comprising voxels of the parameterized voxel-based model, and, by a quantitative MRI modelling technique, constructing the parameters for the respective voxels of the parameterized voxel-based model.

The MRI volume scans are obtained from, for example, an MRI scanner. The at least two weighted MRI volume scans are obtained with, for example, two different slices of the tissue, or for two different spatial orientations of slices, or slices that are shifted with respect to each other. The at least two weighted MRI volume scans each comprise distinct data with respect to each other.

The weighted MRI volume scans may comprise distinct scans comprising varying diffusion weighted strengths, also known as b-value. The weighted MRI volume scans may also be obtained using tensor-valued diffusion encoding facilitated by Q-space trajectory imaging, which enables variable diffusion weighting shapes such as planar and spherical encoding. Thus, the MRI scans may be obtained by changing diffusion weighting strength, diffusion weighting direction and diffusion weighting shape. This way the dimensionality of the diffusion measurement space increases.

Subsequently, the obtained weighted MRI volume scans are transformed into parameters of a parameterized voxel-based model. The parameterized voxel-based model is a model of the tissue, whereby parameters thereof describe properties of the tissue. The transforming of the weighted MRI volume scans into the parameters is performed by combining a super-resolution imaging technique with a quantitative MRI modelling technique.

The super-resolution imaging technique processes the weighted MRI images into a volume comprising voxels, whereby the resolution of the volume is upscaled with respect to the individual weighted MRI images.

In a combined performed manner, the quantitative MRI modelling technique constructs parameters for the respective voxels of the parameterized voxel-based model and is performed for each voxel separately.

The combined performing means that the constructing is performed in an iterative process, thus by alternatively constructing the volume comprising the voxels on the one hand, and the parameters in the voxels on the other hand, such that both the volume and the parameters converges to the parameterized voxel-based model. When converged, for example when meeting a convergence condition, the voxels in the volume comprises parameters which describe the tissue at a resolution that is greater than or equal to that of the input MRI scans.

Since the quantitative MRI modelling technique is applied on weighted MRI volume scans per voxel through the combined performing in an iterative manner, it is an advantage that a modelling per voxel converges in a faster manner compared to modelling all voxels simultaneously. Furthermore, imposing constraints for optimization per voxel lead to a solution in a faster manner then simultaneously imposing them on all voxels. At the same time the number of parameters of the quantitative MRI modelling technique is retained, thus higher compared to the diffusion tensor model. Furthermore, since the volume is constructed by the super-resolution imaging technique, more voxels are constructed as well, leading to more parameters describing the tissue without the need of increasing the acquisition time and/or reducing the SNR. In other words, the trade-off is leveraged without leveraging any of the elements thereof.

Furthermore, by using the super-resolution imagining technique, a motion, geometric transformation, blurring, and/or down-sampling of the different DW images when obtaining them, is taken into account.

When using tensor-valued diffusion encoding, typically echo times are longer. This may lead to lower SNR and/or longer overall scan times. However, the advantage of using the super-resolution technique is that these drawbacks of lower SNR and/or longer scan times are overcome.

Since the transforming is performed by using weighted MRI volume scans, the method is suitable for, among others, scalar MRI, diffusion MRI, relaxometry, perfusion MRI and functional MRI.

According to an embodiment, the combined performing comprises:
  calculating by an outer loop a residual based on an approximated set of the parameters; and wherein the calculating further comprises sequentially determining the approximated set by the quantitative MRI modelling technique respectively the super-resolution imaging technique thereby obtaining the residual; and
  updating by an inner loop the approximated set with the residual by the quantitative MRI modelling technique In other words, the combined performing may be initiated by approximating the parameters by an approximated set, which may initially set at zero. Next, this approximated set is transformed into approximated high-resolution weighted MRI volume images by the quantitative MRI modelling technique, which are, subsequently, downscaled by the super-resolution imaging technique into predicted low-resolution weighted MRI volume images. These predicted low-resolution weighted MRI volume images are compared with the obtained weighted MRI volume images, thereby, in case, obtaining a difference between them. This difference is then upscaled by the super-resolution imaging technique resulting in the residual which relates to the high-resolution weighted MRI volume images. The residual is thus indicative to which extend the approximated set corresponds to the parameters of the tissue.

Next, the inner loop transforms per voxel the residual by the quantitative MRI modelling technique into residual high-resolution parameters for updating the approximated set of the outer loop.

The outer loop thus comprises an iterative back projection, which has the advantage that there is no need to calculate first- and second-order partial derivates. Secondly, there is also no need to impose optimization constraints, such that the outer loop is performed in an efficient and straightforward manner.

Further, since the inner loop transforms the residual per voxel independently, it may be performed using any solver, and potential constraints may be satisfied easily compared to satisfying constraints for all voxels simultaneously. As a result, the combined inner and outer loop converges in a fast way.

According to an embodiment, the combined performing is performed until the residual is less than a predefined convergence threshold.

Differently formulated, the outer loop and the inner loop are iteratively repeated until the residual is less than a predefined convergence threshold, thus until the approximated set of the parameters corresponds sufficiently accurate to the parameters as determined by the threshold. Advantageously, in this way the trade-off may further be made by setting the threshold to a level corresponding to the desired accuracy.

According to an embodiment, the inner loop further comprises imposing optimization constraints on the parameterized voxel-based model.

The optimization constraints are, for example, constraints to preserve a non-negativity of the parameters and may, for example, be imposed each time the inner loop transforms the residual by verifying that the updated set comprises non-negativity parameters. This way, it is avoided that the combined performing results to negative parameters, which do not correspond to real-life characteristics of the tissue.

Furthermore, since the inner loop is performed per voxel, the combined performing will easily satisfy to the imposed constraints.

According to an embodiment, the weighted MRI volume scans comprises DW images; and the quantitative MRI modelling technique comprises a multi-compartment spherical deconvolution technique.

The method is thus also suitable for obtaining DW images from a dMRI scanner, an MRI scanner comprising a functionality to perform dMRI scans, or from another apparatus suitable for collecting DW images. At least two DW images are thus likewise obtained, for example from two different shifted slices, or slices with different spatial orientations.

When transforming the DW images, a spherical deconvolution technique may be applied. Thus, the transforming then comprises transforming the DW images into parameters of the parameterized voxel-based model of the tissue by combined performing by the super-resolution imaging technique, constructing a volume comprising voxels of the parameterized voxel-based model, and, by the spherical deconvolution technique, constructing parameters for the respective voxels of the parameterized voxel-based model such that the parameters correspond to the parameters of the voxels in the volume when deconvolved.

The outer loop then comprises calculating a residual based on an approximated set of the parameters; and wherein the calculating further comprises sequentially convolving and scaling the approximated set by the spherical convolution technique respectively the super-resolution imaging technique thereby obtaining the residual.

The inner loop then approximates the set by deconvolving the residual by the spherical deconvolution technique.

According to an embodiment, the DW images comprises at least images according to at least two orientations and two strengths of a diffusion sensitizing gradient.

When obtaining the DW images, the diffusion sensitizing gradient for causing the diffusion of water-molecules in the examined tissue is thus oriented in at least two orientations. This way, anisotropic characteristics of the tissue may be identified.

Furthermore, the diffusion sensitizing gradient is also imposed for different strengths. This way, likewise, isotropic characteristics of the tissue may be identified in a more accurate way.

According to an embodiment, the parameters describe functions on spheres.

The parameters per voxel may thus describe functions on a sphere by, for example, basis functions describing a function on the sphere. These functions on the sphere are thus indicative for the parameters in the tissue.

According to an embodiment, the parameters comprise spherical harmonics.

This way, the deconvolution of the spheres in harmonics may be performed in a straightforward manner. Furthermore, a path and location of axons, such as neural axons, of a fibre in the tissue may be identified as well.

According to an embodiment, the parameters comprise fibre-orientation distribution functions, fODF.

The fibre-orientation distribution functions describe the tissue by a fODF orientation and a fODF amplitude. The fODF's main orientations are indicative for local fibre orientations in the tissue and the fODF amplitudes are indicative for a tract-specific quantitative biomarker of the intra-cellular volume of the tissue.

According to an embodiment, the tissue comprises brain tissue, and wherein the fODF are indicative for properties of WM in the brain tissue.

Thus, besides the amplitudes, the fODF are further indicative for properties of the WM, like a presence and a distribution thereof, in the brain tissue.

According to an embodiment, the parameters are indicative for properties of a WM density, a GM density and/or a CSF density.

In other words, the brain tissue may be described in a very accurate manner by interpreting the parameters as a distribution of densities of respectively WM, GM and/or CSF.

According to a second aspect, the disclosure relates to a data processing apparatus comprising means for carrying out the method according to the first aspect.

According to a third aspect, the disclosure relates to a computer program comprising instructions, which, when the program is executed by a computer, cause the computer to carry out the method according to the first aspect.

According to a fourth aspect, the disclosure relates to a computer-readable data carrier having stored thereon the computer program of the third aspect.

According to a sixth aspect, the disclosure relates to magnetic resonance imaging scanner comprising the data processing apparatus according to the second aspect.

BRIEF DESCRIPTION OF THE DRAWINGS

Some example embodiments will now be described with reference to the accompanying figures.

DETAILED DESCRIPTION OF EMBODIMENT(S)

Figure 4:
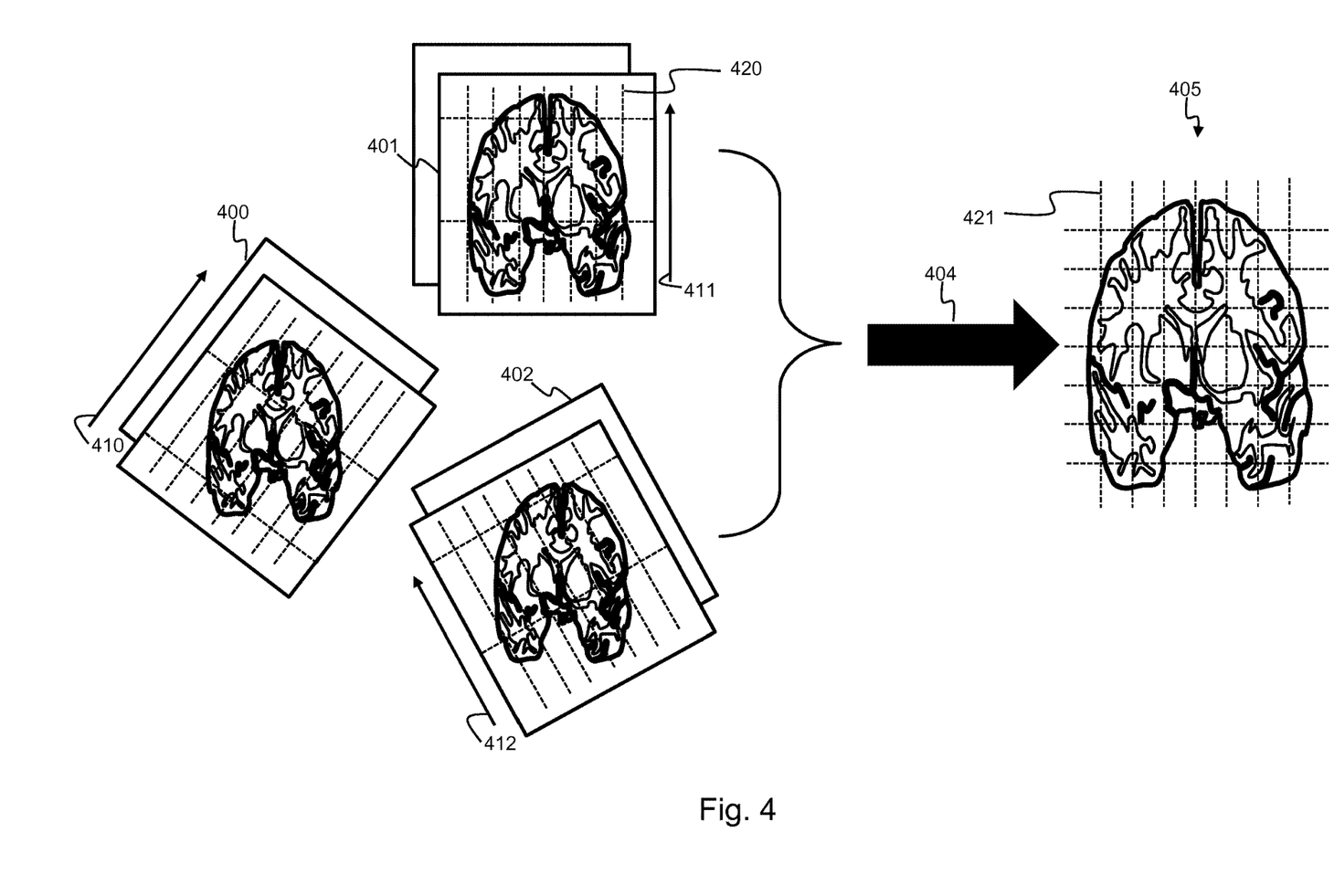
FIG. 4 illustrates a set of DW images transformed into a parameterized voxel-based model according to an example embodiment.
Figure 5:
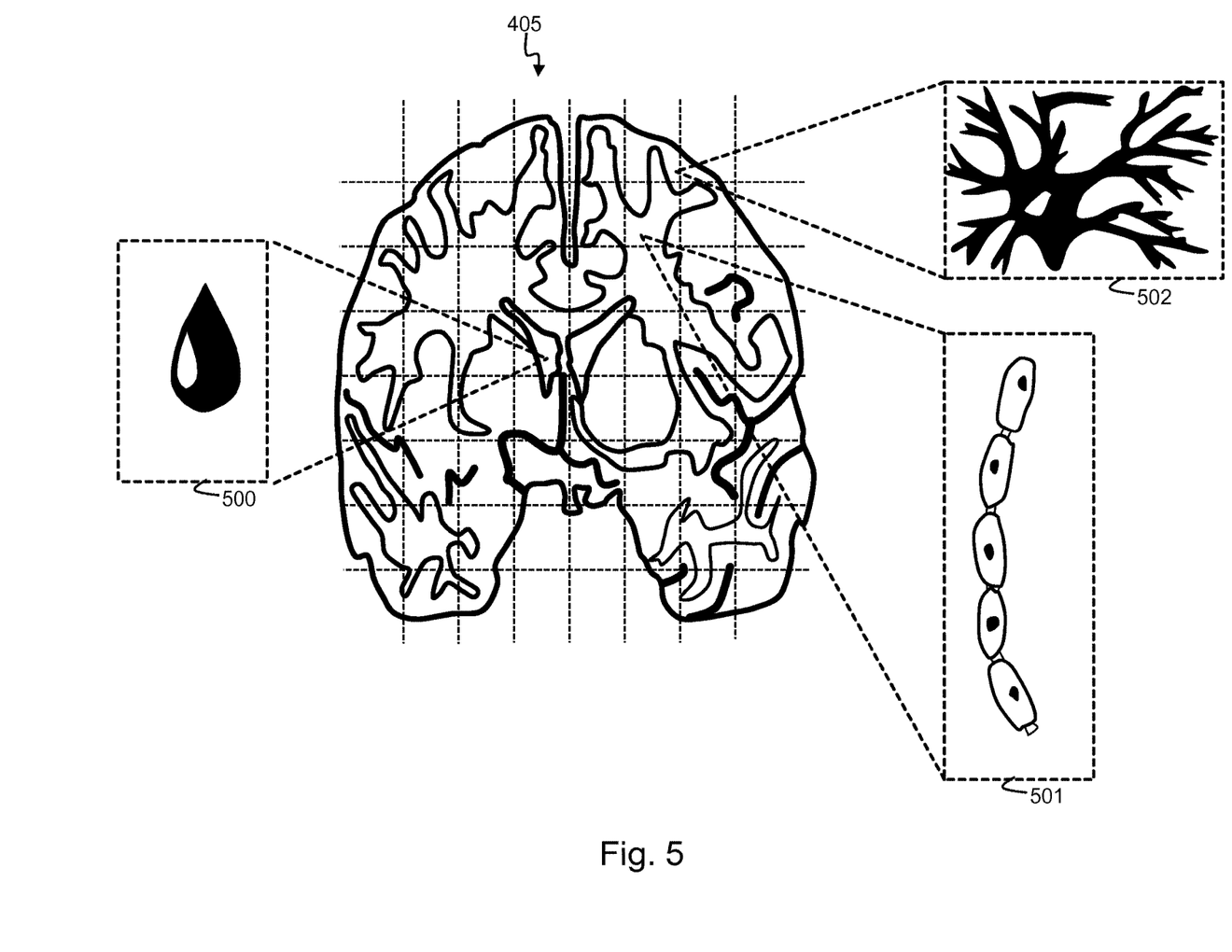
FIG. 5 illustrates an example of a brain tissue illustrating properties of a brain.
Figure 6:
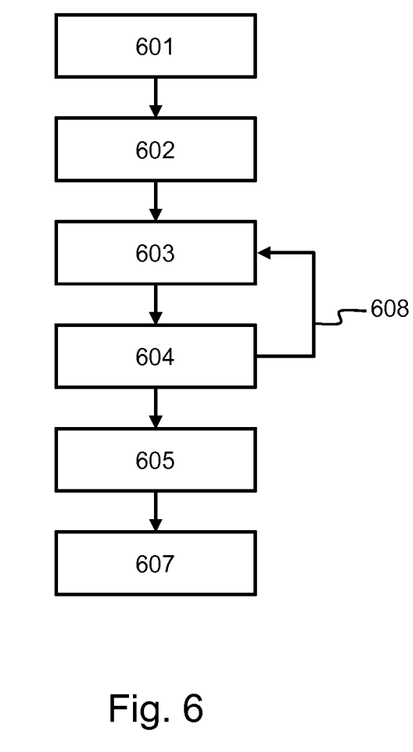
FIG. 6 illustrates an example embodiment of steps performed by a computer-implemented method for determining a parameterized voxel-based model.

FIG. 6 illustrates an example embodiment of steps 601-608 performed by a computer-implemented method for obtaining DW images and transforming the DW images into a parameterized voxel-based model. These steps will be further illustrated by reference to FIGS. 1 to 5 showing different intermediate results and representations of a brain tissue when the transformation process is performed, as an example, on such a brain tissue.

Figure 1:
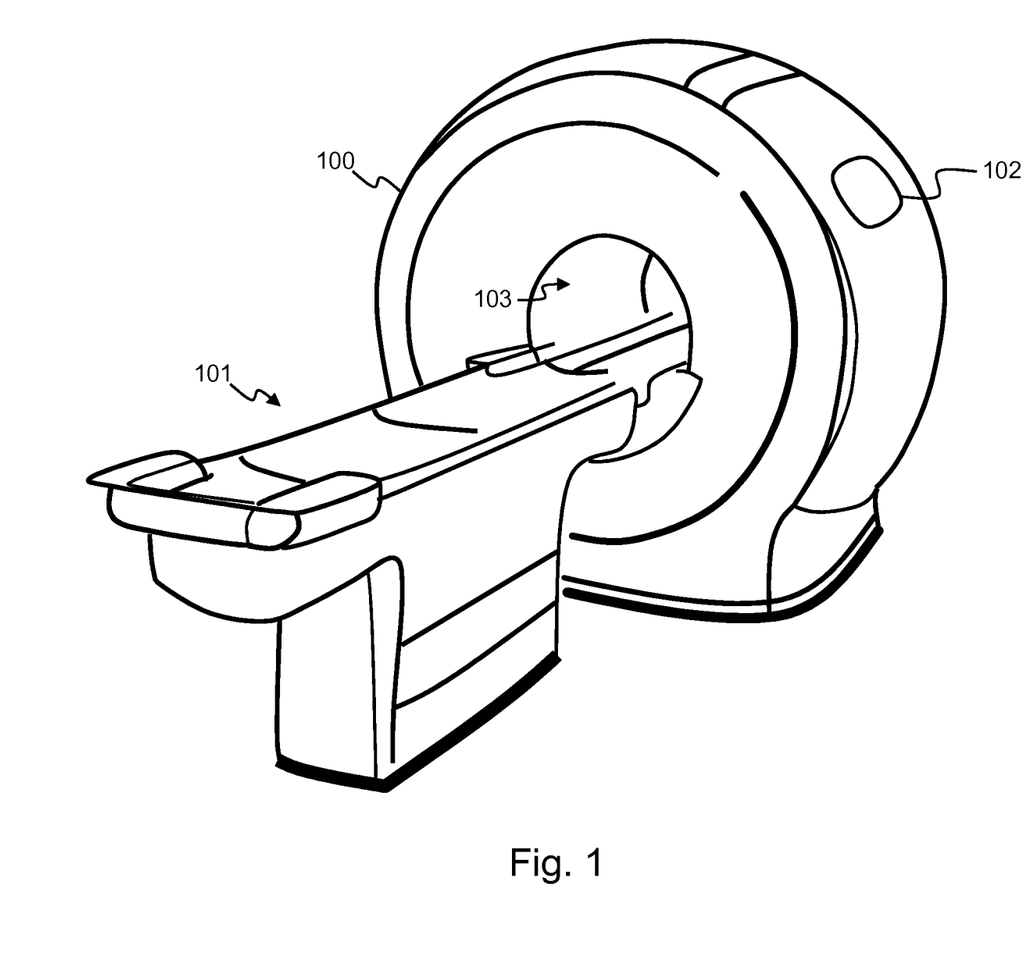
FIG. 1 illustrates an example embodiment of an MRI scanner comprising a data processing apparatus for obtaining and transforming DW images.
Figure 2:
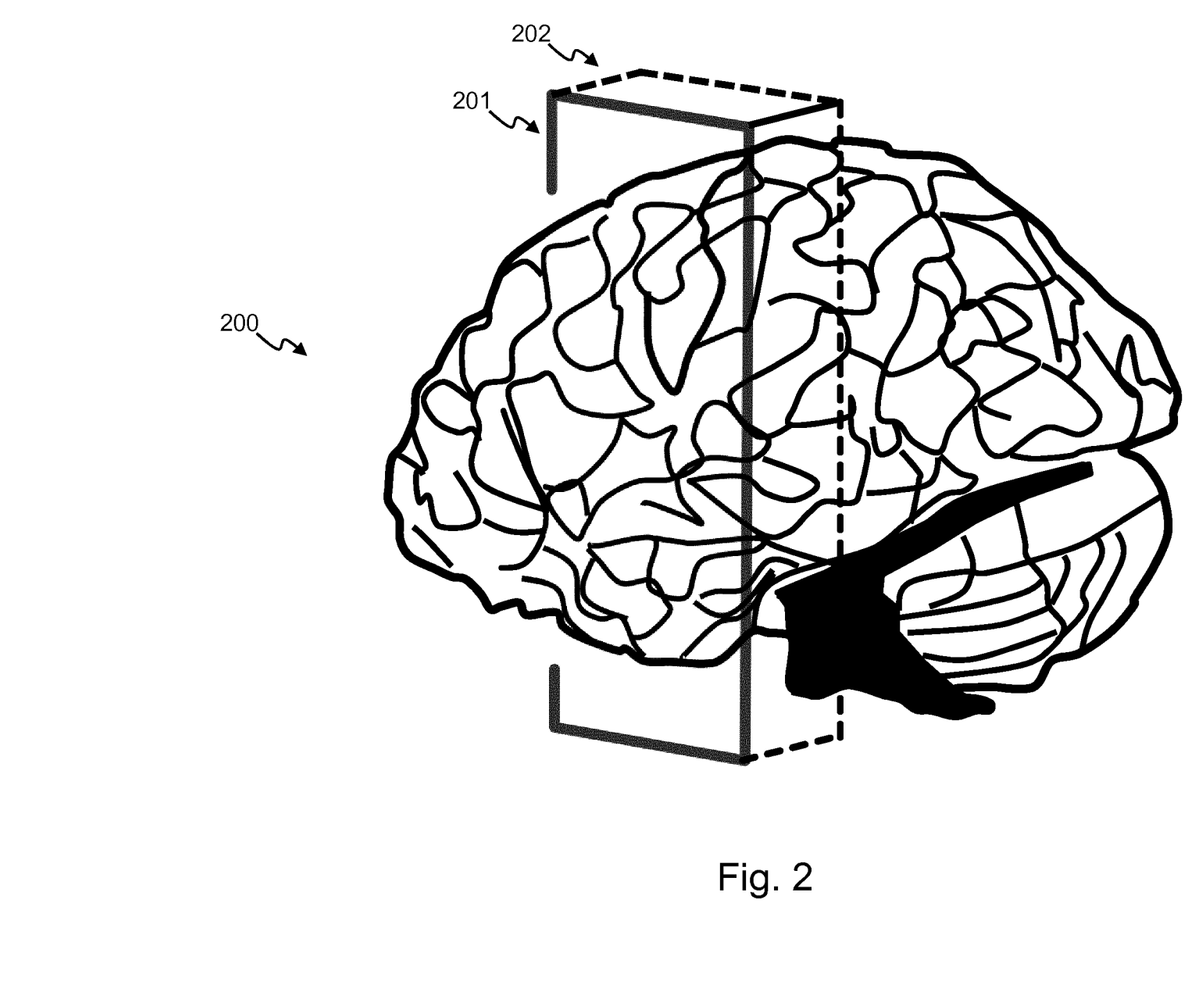
FIG. 2 illustrates an example of a brain tissue from which DW images are obtained according to an example embodiment.

In a first step, DW images are obtained 601 from a tissue, such as for example brain tissue 200 as illustrated in FIG. 2. DW images are a type of volume scans comprising a three-dimensional representation of a tissue. To obtain the images, a patient may lay down on a platform 101 of an MRI scanner 100 as illustrated in FIG. 1. This may be done such that the patient's head is in the zone 103 where measurements by the MRI scanner 100 are performed. These measurements result in DW images 400-402 as shown in FIG. 4 which are, for example, collected by a data processing apparatus 102. The data processing apparatus 102 may be integrated in the MRI scanner 100, or may, for example, be located on a remote place compared to the MRI scanner 100, and/or performs steps and associated calculations in the cloud.

Figure 3:
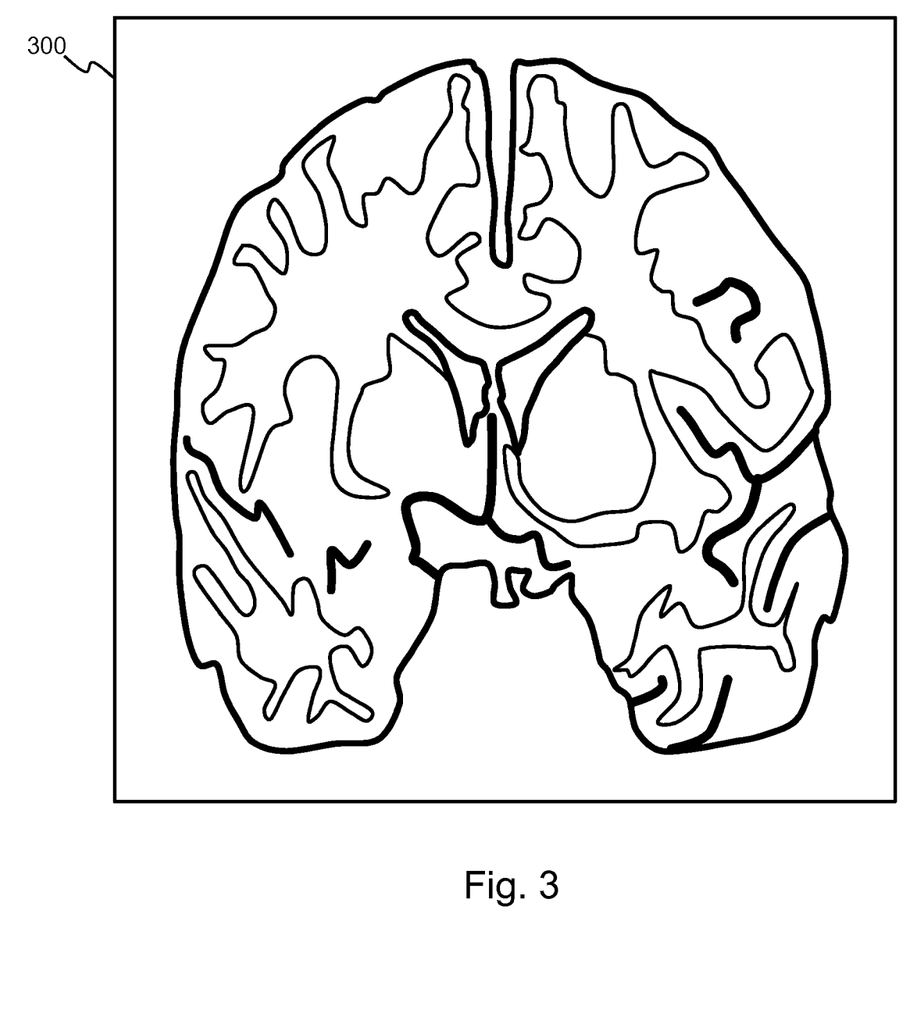
FIG. 3 illustrates DW images obtained according to an example embodiment.

Of the brain tissue 200 different DW images for different slices are obtained. An example of a slice is illustrated by slice 201, which has a thickness 202. From the slice 201 a DW image 300, of which an example is illustrated in FIG.

3, is obtained in step 601. A DW image, such as DW image 401 is a view perpendicular on the slice 201. The obtaining 601 is performed for different slices and different orientations, as illustrated by DW images 400, 401, and 402. For DW image 400, the slice direction is illustrated by direction 410, for DW image 402, the slice direction is illustrated by direction 412, and for DW image 401, the slice direction is illustrated by direction 411. Alternatively, DW images may also be obtained by shifting the slices instead of changing the direction.

A slice may comprise a high thickness, thus a slice comprising a major part of the brain 200, comprising a DW image with a high SNR. This way, only a limited number of slices needs to be obtained from the brain 200 to cover it, which may be obtained in a fast manner, such that a patient does not have to lay down too long on a platform 101, or in a same time period more data may be obtained leading to a higher precision of the resulting quantitative parameters.

The DW images are obtained at a low resolution, as illustrated by grid 420 for DW image 401, and combined by a transformation operation 404 into a parameterized voxel-based model 405 by applying the steps of FIG. 6. The transformation is done such that the resolution of the parameterized voxel-based model 405 is higher compared to the individual DW images 400, 401, 402. This is illustrated by grid 421 of the parameterized voxel-based model 405. The higher resolution is not obtained by an upscaling operation but by the information that is embedded in the different orientations of the lower resolution input DW images.

When obtaining the DW images, the dMRI scanner may vary these different orientations of the diffusion sensitizing gradient of over a complete sphere.

Furthermore, per orientation, the strength of the diffusion sensitizing gradient may be varied as well, thereby leading to a set of DW images comprising a range of contrasts. Alternatively, the diffusion sensitizing gradient may also be encoded by a tensor.

When encoded by a tensor, q-space trajectory imaging, QTI, facilitates tensor-valued diffusion encoding with variable shapes, such as planar and spherical encoding, which may provide information not available with conventional stick shaped b-tensors. Further, by assuming that the diffusion in heterogeneous tissue can be modelled by a diffusion tensor distribution, DTD, the addition of b-tensors with different shapes can be used to disentangle variation in diffusivity from variation in microscopic anisotropy and orientation dispersion. This provides more specific parameters than those available from conventional diffusion MRI.

Per slice orientation or slice shift, the weighting strength and weighting orientation of the diffusion sensitizing gradient of the scanner may also by varied. For example, per orientation, four weighting strengths are used with four individual weighting orientations, such that the total amount of obtained DW images is, in this example embodiment, sixty-four.

Another example of obtaining DW images when using QTI are five DW data sets with spatial resolution 2×2×6 mm$^3$, each with a unique slice rotation=[−72°,−36°,0°,36°, 72°], targeting 2×2×2 mm$^3$ super-resolution reconstruction. Each DW data set contains a unique set of thirty-one samples of combining b=[0.1,1,2] ms/μm$^2$, and linear, planar, and spherical tensor encoding shapes. This results in one hundred and fifty-five unique samples across all rotations. The ratio repetition time over echo time is 3900 ms/91 ms, which results in a total acquisition time of approximately ten minutes.

The DW images are combined by transforming 404, them into a voxel-based parameterized model 405 of the brain 200 tissue. The transforming 404 is, amongst other steps 605, 606 and 607, performed through a combined 608 performing of an outer loop 603 and an inner loop 604.

The outer loop 603 solves a complete optimization problem and performs iterative back projections. First, its start with an approximated set of parameters $\hat{x}_{HR}$ at a high-resolution, HR, which, to initiate the loop, may be set at zero. Next, the HR approximated or predicted set is voxel-wise convolved by a voxel-wise multi-tissue spherical convolution matrix C into HR predicted DW images $\widetilde{DWI}_{HR}$.

In a next step of the outer loop 603, the HR predicted DW images $\widetilde{DWI}_{HR}$ are transformed volume-wise by a geometric transformation through a matrix S of a super-resolution imaging technique into low-resolution, LR, DW images $\widetilde{DWI}_{LR}$.

Subsequently, from the LR DW images $\widetilde{DWI}_{LR}$ a residual is calculated by comparing the LR DW images $\widetilde{DWI}_{LR}$ with the obtained 601 DW images 400, 401, 402. The residual thus represents to which extent the predicted LR DW images $\widetilde{DWI}_{LR}$ corresponds to the obtained DW images.

Next, the calculated residual $\widetilde{DWI}_{LR}$ RES is volume-wise transformed by a transpose geometric transformation to a HR residual $DWI_{HR\_RES}$. This HR residual $DWI_{HR\_RES}$ is then used as an input to the inner loop 604.

The outer loop 603 may be further illustrated by the following pseudo-code:

$\hat{x}_{HR}=0$;
for i=1:N$_{max}$
   [C]*$\hat{x}_{HR}$*→$\widetilde{DWI}_{HR}$
   [S]*$\widetilde{DWI}_{HR}$→$\widetilde{DWI}_{LR}$
   $DWI_{LR\_RES}=\widetilde{DWI}_{LR}-DWI_{LR}$
   [S]$^T$*$DWI_{LR\_RES}$→$DWI_{HR\_RES}$
   inner loop 604
   $\hat{x}_{HR}+=\hat{x}_{HR\_RES}$
end;

wherein N$_{max}$ is a value depending on a preferred accuracy, or on a predefined convergence threshold.

It is not required that the outer loop 603 has to take into account constraints or has to perform an inversion of the matrix C or S. Further, since it uses back projection, it does not require a gradient or Hessian.

The inner loop 604 receives from the outer loop 603 a calculated HR residual $DWI_{HR\_RES}$, which is on its turn transformed into a HR residual of the set of parameters $x_{HR\_RES}$. This calculated HR residual of the set of parameters $x_{HR\_RES}$ is then send back 608 to the outer loop 603 to update the predicted set of parameters $\hat{x}_{HR}$ by $\hat{x}_{HR}+=\hat{x}_{HR\_RES}$ in a next iteration of the outer loop 603.

The inner loop 604 calculates the HR residual of the set of parameters $x_{HR\_RES}$ by voxel-wise deconvolution of the HR residual $DWI_{HR\_RES}$ by solving a constrained linear least squares problem of the form $$\hat{x}_{HR\_RES} = \underset{x}{\mathrm{argmin}} \|Cx - d\|_2^2,$$

with d=$DWI_{HR\_RES}$, with constraints imposing a non-negativity of physical properties of the tissue, like, for example a GM density.

When obtaining the DW images using QTI, the DTD may likewise be estimated voxel-wise and can also be cast as a least square problem of the form $$\hat{x} = \underset{x}{\mathrm{argmin}} \, \|\exp(Bx) - y\|_2^2$$

subject to $Cx \geq 0$, where $\exp(Bx)$ is the forward modelling operation relating to the log of the non-diffusion-weighted signal, the diffusion tensor distribution, DTD, mean and the DTD covariance, represented in parameter vector x, to the vector of measured dMRI intensities y. The constraint matrix C enforces non-negative diffusivities and kurtoses as well as monotonic signal decay with increasing b-value. The form of the equation can also be extended to support volume-wise super resolution estimation of the QTI parameters as $$\hat{x}' = \underset{x'}{\mathrm{argmin}} \, \|A \, \exp(Bx) - y'\|_2^2$$

subject to $C'x' \geq 0$, where $\exp(B'x)$ is the volume-wise forward modelling operation and A is the super-resolution sampling matrix, relating the signal intensities expected in the high-resolution voxels to the acquired DW signal intensities in all low-resolution voxels, y', and C' is the volume-wise constraint matrix.

The inner loop 604 may solve the voxel-wise spherical deconvolution, in case with constraints, using a normal quadratic programming solver. The inner loop 604 may be solved for each voxel independently, like a normal data set without super resolution. Because this step is voxel-wise, it requires hardly any memory, it converges very fast and easily satisfies the constraints.

The outer loop 603 and the inner loop 604 are combined 608 until a residual, for example residual $\hat{x}_{HR\_RES}$ is less than a predefined threshold.

As a result, a parameterized voxel-based model 405 is calculated 605, of which the resolution is higher than the individual DW images 400, 401, 402. This parameterized voxel-based model 405 comprises voxels comprising functions of the sphere or spherical functions. These spheres are indicative for properties of the brain tissue 200, like the presence of white matter, WM 501, gray matter, GM 502, and/or cerebrospinal fluid, CSF 500, and may further be described as orientation distribution functions of these properties.

The spheres per voxel in the parameterized voxel-based model 405 are describing spherical harmonics. The spherical harmonics are special functions defined on the surface of a respective sphere.

Real and symmetric spherical functions such as the fODF are represented as a linear combination of modified spherical harmonic basis functions or spherical basis functions. The fODF orientations can then be used to track long-range connections of the brain tissue 200 using fibre tracking for, for example, planning neurosurgery. The fODF amplitudes can serve as a tract-specific quantitative biomarker for the intra-cellular volume of WM axons for, for example, studying brain development or neurodegeneration.

As a result, the brain tissue 200 is characterized by step 607 by a set of parameters comprising, for example, forty-seven parameters, which is considerably higher compared to a diffusion tensor model. The forty-seven parameters comprise forty-five spherical coefficients describing WM 501 fODF, a coefficient describing an amount of GM 502, and one coefficient describing an amount of CSF 500. The forty-five spherical coefficients are a number of real and symmetric spherical harmonics basis functions for a spherical harmonic basis of order eight, which may further be varied.

Figure 7:
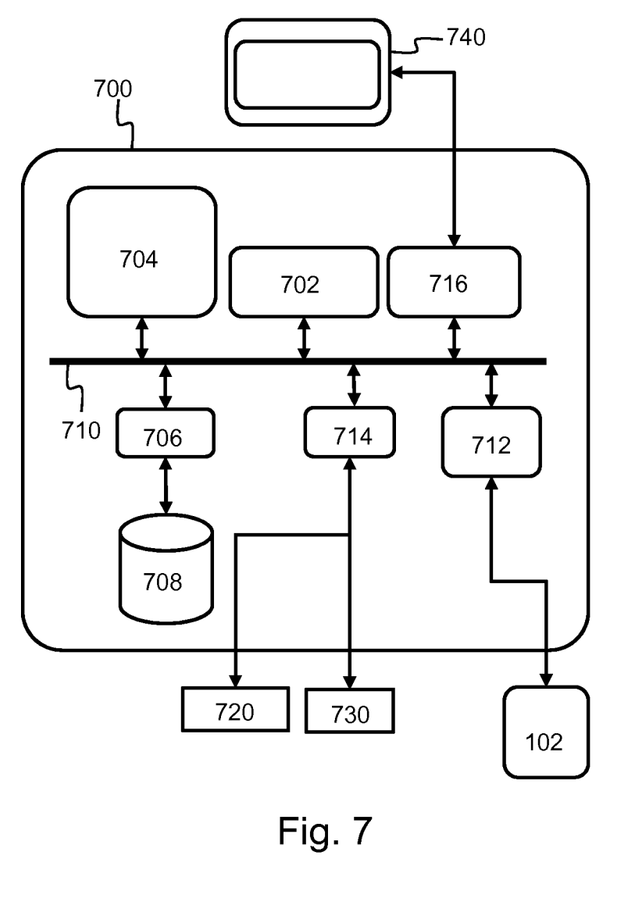
FIG. 7 illustrates a suitable computing system for performing steps according to example embodiments.

FIG. 7 shows a suitable computing system 700 according to an example embodiment. Computing system 700 comprises means for performing the steps according to the above example embodiments. Computing system 700 may therefore be used as suitable implementation of data processing apparatus 102. Computing system 700 may in general be formed as a suitable general-purpose computer and comprise a bus 710, a processor 702, a local memory 704, one or more optional input interfaces 714, one or more optional output interfaces 716, a communication interface 712, storage element interface 706 and one or more storage elements 708. Bus 710 may comprise one or more conductors that permit communication among the components of the computing system 700. Processor 702 may include any type of conventional processor or microprocessor that interprets and executes programming instructions. Local memory 704 may include a random-access memory (RAM) or another type of dynamic storage device that stores information and instructions for execution by processor 702 and/or a read only memory (ROM) or another type of static storage device that stores static information and instructions for use by processor 702. Input interface 714 may comprise one or more conventional mechanisms that permit an operator to input information to the computing device 700, such as a keyboard 720, a mouse 730, a pen, voice recognition and/or biometric mechanisms, etc. Output interface 716 may comprise one or more conventional mechanisms that output information to the operator, such as a display 740, etc. Communication interface 712 may comprise any transceiver-like mechanism such as for example one or more Ethernet interfaces that enables computing system 700 to communicate with other devices and/or systems. The communication interface 712 of computing system 700 may be connected to such another computing system by means of a local area network (LAN) or a wide area network (WAN) such as for example the internet. Storage element interface 706 may comprise a storage interface such as for example a Serial Advanced Technology Attachment (SATA) interface or a Small Computer System Interface (SCSI) for connecting bus 710 to one or more storage elements 708, such as one or more local disks, for example SATA disk drives, and control the reading and writing of data to and/or from these storage elements 708. Although the storage elements 708 above is described as a local disk, in general any other suitable computer-readable media such as a removable magnetic disk, optical storage media such as a CD or DVD-ROM disk, solid state drives, flash memory cards, . . . may be used.

Although the present invention has been illustrated by reference to specific embodiments, it will be apparent to those skilled in the art that the invention is not limited to the details of the foregoing illustrative embodiments, and that the present invention may be embodied with various changes and modifications without departing from the scope thereof. The present embodiments are therefore to be considered in all respects as illustrative and not restrictive, the scope of the invention being indicated by the appended claims rather than by the foregoing description, and all changes which come within the scope of the claims are therefore intended to be embraced therein.

It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", "third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above

The invention claimed is:

1. A computer implemented method for obtaining parameterized characteristics of a tissue comprising:
    obtaining at least two weighted magnetic resonance imaging, MRI, volume scans of the tissue;
    transforming the at least two weighted MRI volume scans into a parameterized voxel-based model of the tissue by combined performing, by a super-resolution imaging technique, constructing a volume comprising voxels of the parameterized voxel-based model, and, by a quantitative MRI modelling technique, constructing parameters for the respective voxels of the parameterized voxel-based model; and
    generating an image of the tissue from the parameterized voxel-based model;
    wherein the combined performing comprises:
        calculating by an outer loop a residual based on an approximated set of the parameters for the respective voxels, wherein the calculating further comprises sequentially determining the approximated set by the quantitative MRI modelling technique and respectively the super-resolution imaging technique thereby obtaining the residual; and
        updating by an inner loop the approximated set with the residual by the quantitative MRI modelling technique;
    wherein the combined performing is performed until the residual is less than a predefined convergence threshold.

2. The computer implemented method according to claim 1, wherein the inner loop further comprises imposing optimization constraints on the parameterized voxel-based model.

3. The computer implemented method according to claim 1, wherein the weighted MRI volume scans comprise diffusion weighted images; and
    wherein the quantitative MRI modelling technique comprises a multicompartment spherical deconvolution technique.

4. The computer implemented method according to claim 3, wherein the diffusion weighted images comprise images according to at least two orientations and at least two strengths of a diffusion sensitizing gradient.

5. The computer implemented method according to claim 1, wherein the parameters describe functions on spheres.

6. The computer implemented method according to claim 1, wherein the parameters comprise spherical harmonics.

7. The computer implemented method according to claim 1, wherein the parameters comprise fibre-orientation distribution functions.

8. The computer implemented method according to claim 1, wherein the tissue comprises a brain tissue, and
    wherein the fibre-orientation distribution functions are indicative for properties of white matter in the brain tissue.

9. The computer implemented method according to claim 8, wherein the parameters are indicative for properties of the white matter density, a gray matter density, and/or a cerebrospinal fluid density.

10. A data processing apparatus comprising at least a processor and a non-transitory memory configured for carrying out the method according to claim 1.

11. A magnetic resonance imaging scanner comprising the data processing apparatus according to claim 10.

12. A non-transitory computer-readable data carrier having stored thereon a computer program comprising instructions which, when the program is executed by a computer, cause the computer to carry out the method according to claim 1.

* * * * *